United States Patent
Kim et al.

(10) Patent No.: US 11,273,000 B2
(45) Date of Patent: Mar. 15, 2022

(54) STEREOTACTIC DEVICE FOR PRIMATE BRAINS

(71) Applicants: KOREA RESEARCH INSTITUTE OF CHEMICAL TECHNOLOGY, Daejeon (KR); GWANGJU INSTITUTE OF SCIENCE AND TECHNOLOGY, Gwangju (KR)

(72) Inventors: Hyung Sun Kim, Gwangju (KR); Su Cheol Han, Jeollabuk-do (KR); Dong Ho Woo, Chungcheongnam-do (KR); Young Su Yang, Gwangju (KR); Goo Hwa Kang, Jeollabuk-do (KR); Hyung Ihl Kim, Gwangju (KR); Ji Young Park, Gwangju (KR); Dong Hak Byun, Gwangju (KR)

(73) Assignees: KOREA RESEARCH INSTITUTE OF CHEMICAL TECHNOLOGY, Daejeon (KR); GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 677 days.

(21) Appl. No.: 16/321,012

(22) PCT Filed: Jul. 19, 2018

(86) PCT No.: PCT/KR2018/008173
§ 371 (c)(1),
(2) Date: Jan. 25, 2019

(87) PCT Pub. No.: WO2019/017711
PCT Pub. Date: Jan. 24, 2019

(65) Prior Publication Data
US 2019/0175299 A1    Jun. 13, 2019

(30) Foreign Application Priority Data
Jul. 19, 2017   (KR) .................. 10-2017-0091708

(51) Int. Cl.
*A61B 90/14* (2016.01)
*A61B 5/00* (2006.01)
(Continued)

(52) U.S. Cl.
CPC ............... *A61B 90/14* (2016.02); *A61B 5/00* (2013.01); *A61B 5/702* (2013.01); *A61B 90/13* (2016.02);
(Continued)

(58) Field of Classification Search
CPC ......... A61B 34/30; A61B 34/37; A61B 34/20; A61B 34/71; A61B 34/70; A61B 90/361;
(Continued)

(56) References Cited

U.S. PATENT DOCUMENTS

2004/0260311 A1* 12/2004 Bourel ................. A61B 90/39
606/130

FOREIGN PATENT DOCUMENTS

| JP | 2693195 B2 | 12/1997 |
|----|-----------|---------|
| KR | 10-0647491 B1 | 11/2006 |

(Continued)

OTHER PUBLICATIONS

International Search Report for PCT/KR2018/008173 dated Oct. 19, 2018 and its English translation from WIPO (now published as WO 2019/017711 A1).
(Continued)

*Primary Examiner* — Katherine M Shi
(74) *Attorney, Agent, or Firm* — Ladas & Parry, LLP (57) ABSTRACT

A stereotactic device for primate brains indicates a brain coordinate reference point of a primate using a simulator for indicating a brain coordinate reference point, thereby providing an initial setting to a zero point corresponding to the brain coordinate reference point. The brain coordinate reference point is conveniently and accurately indicated with-
(Continued)

out relatively expensive equipment, such as a magnetic resonance imaging (MRI) scanner, to determine brain coordinates of the primate, so that a targeting procedure can be conducted on the brain.

15 Claims, 8 Drawing Sheets

(51) Int. Cl.
*A61B 90/13* (2016.01)
*A61B 90/10* (2016.01)
*A61B 90/50* (2016.01)
*A61B 90/57* (2016.01)

(52) U.S. Cl.
CPC ... *A61B 2090/101* (2016.02); *A61B 2090/508* (2016.02); *A61B 2090/571* (2016.02); *A61M 2210/0687* (2013.01)

(58) Field of Classification Search
CPC ............ A61B 90/11; A61B 2034/2055; A61B 90/10–14; A61B 2090/101–103
USPC ......................................................... 606/130
See application file for complete search history.

(56) References Cited

FOREIGN PATENT DOCUMENTS

| KR | 10-0977909 B1 | 8/2010 |
|---|---|---|
| KR | 10-2012-0068426 A | 6/2012 |
| KR | 10-1406216 B1 | 6/2014 |

OTHER PUBLICATIONS

Written Opinion of the International Searching Authority for PCT/KR2018/008173 dated Oct. 19, 2018 and its English translation by Google Translate (now published as WO 2019/017711 A1).

* cited by examiner

STEREOTACTIC DEVICE FOR PRIMATE BRAINS

CROSS-REFERENCE TO RELATED APPLICATIONS

This application is the U.S. National Stage of International Patent Application No. PCT/KR2018/008173 filed on Jul. 19, 2018, which claims the priority to Korean Patent Application No, 10-2017-0091708 filed in the Korean Intellectual Property Office on Jul. 19, 2017, the entire contents of which are incorporated herein by reference.

TECHNICAL FIELD

The present disclosure relates to a stereotactic device for primate brains. More particularly, the present disclosure relates to a stereotactic device for primate brains, which can indicate a brain coordinate reference point of a primate using a simulator for indicating a brain coordinate reference point, thereby providing an initial setting to a zero point corresponding to the brain coordinate reference point. Accordingly, it is possible to conveniently and accurately indicate the brain coordinate reference point without relatively expensive equipment, such as a magnetic resonance imaging (MRI) scanner, to determine brain coordinates of the primate, so that a targeting procedure can be conducted on the brain.

BACKGROUND ART

Recently, the role and importance of animal testing using non-human primates have been significantly increased, due to activation of the life science and medical science fields, and the development of a range of animal testing facilities is being undertaken in institutes, hospitals, companies, and the like.

Animal testing facilities may be generally categorized as 1) facilities mainly involved in the production of experimental animals (e.g. production facilities of companies), 2) facilities mainly involved in the study of experimental animals (e.g. facilities of institutes), 3) facilities mainly involved in animal testing (e.g. facilities of medical schools or the like), 4) facilities focused on safety testing, and 5) facilities mainly involved in the development of medicines.

Such facilities must provide high quality animals, ensure proper breeding management, maintain and manage suitable testing environments, and be compared based on the persistence of obtained results. It may be most significantly important for experimental animal facilities to guarantee the scientific basis and ethnicity of animal testing.

The level of life science in the Republic of Korea has been steadily and rapidly improved since the 1980s. Some fields, such as developmental biotechnology, are internationally recognized as being in leading positions. However, compared to the progress of research and the application of testing animals, overall conditions, such as facilities related to the management and use of experimental animals, which are the basis of such studies and applications, are at relatively low levels. Activities for the development and advancement thereof are currently significantly insufficient.

In general, experimental animals, such as rodents, non-rodent animals, and primates, have played significant roles in evaluating the efficacy, as well as safety, such as toxicity, of new medicines and in studying the prevention and treatment of diseases. Such animal testing includes a range of experiments, from simple blood tests to experiments including direct administration of medicine to the brain.

Recently, a number of institutes around the world have been conducting brain studies using rodents. However, the results of the brain studies using rodents must be verified using primates before being applied to humans, since the gap between rodents and humans is too significant.

However, brain studies using primates are still not commonly undertaken, due to the specialties of research primates or monkeys (e.g. rarity, tendencies demanding high technology, problems related to zoonoses, high maintenance costs, and the necessity of the use of relatively expensive equipment and experts).

For brain studies and experiments using primates, a stereotactic device able to fix the heads of primates is required. However, stereotactic devices for primate brains, which are currently in use, are simply configured to fix the heads of primates. For specific procedures, such as the administration of medicine to a specific organization in the brain or electrical stimulation, other equipment, such as an MRI scanner, is used.

Accordingly, an accurate targeting procedure on a brain organization cannot be conducted only with the use of a stereotactic device for primate brains, without the use of relatively expensive equipment, such as an MRI scanner. In particular, an ear bar zero (EBZ) point (i.e. a center of an imaginary straight line connecting the pair of ears) is generally used as a reference point for a brain organization of a primate. Since the EBZ point is located in an inner area of the brain organization, which cannot be visually recognized, the reference point cannot be determined using a typical stereotactic device for primate brains, thereby making a targeting procedure impossible.

DISCLOSURE

Technical Problem

Accordingly, the present disclosure has been made in consideration of the above-described problems occurring in the related art, and the present disclosure proposes a stereotactic device for primate brains, which can indicate a brain coordinate reference point of a primate using a simulator for indicating a brain coordinate reference point, thereby providing an initial setting to a zero point corresponding to the brain coordinate reference point. Accordingly, it is possible to conveniently and accurately indicate the brain coordinate reference point without relatively expensive equipment, such as a magnetic resonance imaging (MRI) scanner, to determine brain coordinates of a primate, so that a targeting procedure can be conducted on the brain.

Also provided is a stereotactic device for primate brains, which includes an ear bar adaptor that can be fixedly inserted into the ears of the primate during a process of fixing the head of the primate. It is possible to fix the head of the primate to the stereotactic device by inserting the ear bar adaptor into the ears of the primate instead of directly fixing the head of the primate to the stereotactic device. It is thereby possible to more conveniently insert the ear bars into the ears of the primate and determine whether or not the ear bars are accurately inserted in positions.

Also provided is a stereotactic device for primate brains, which includes a carrier body for holding a variety of brain surgery devices. It is possible to conveniently hold and replace a variety of brain surgery devices using a simple configuration without the use of a complicated additional device. Consequently, more various procedures can be more conveniently conducted.

Technical Solution

According to an aspect of the present disclosure, a stereotactic device used for brain experiments on primates may include: a main frame; a pair of ear bars provided on the main frame such that the ear bars are spaced apart from each other in X-axis direction, the pair of ear bars being configured to be inserted into ears of a primate to fix a head of the primate; a movable body disposed movable relative to the main frame; a carrier body connected to the movable body to move integrally with the movable body, and including a laser projector projecting a laser line beam, in a shape of a straight line, along a Y axis extending perpendicular to an X axis; a carriage module connected to the main frame to move the movable body in the X-axis direction, Y-axis direction, and Z-axis direction; and a reference point simulator separably inserted into the main frame to indicate a brain coordinate reference point of the primate, located at a center of an imaginary straight line connecting the pair of ear bars. A position of the movable body is initially set to a zero point corresponding to the brain coordinate reference point, using the laser line beam generated by the laser projector and the brain coordinate reference point indicated by the reference point simulator.

A zero position of the movable body in the X-axis direction may be initially set by moving the movable body using the carriage module such that the laser line beam passes through the brain coordinate reference point.

An engagement recess may be provided in the movable body, and an engagement protrusion may be fixedly provided on the main frame to be inserted into and engaged with the engagement recess. When the engagement recess and the engagement protrusion are engaged with each other, the engagement recess and the engagement protrusion may be disposed in positions in which a zero position of the movable body in the Y-axis direction and the Z axis-direction are initially set. The zero position of the movable body in the Y-axis direction and the Z axis-direction may be initially set by moving the movable body using the carriage module such that the engagement recess and the engagement protrusion are engaged with each other.

One of the pair of ear bars may act as the engagement protrusion.

The movable body may include a movable base, a portion of which is coupled to the carriage module, and an arc portion extending from the movable base to provide an arc section. The engagement recess may be provided in the portion of the movable base.

The carrier body may be movably coupled to the arc portion of the movable body.

A device holder may be replaceably coupled to the carrier body and be configured to hold a brain surgery device.

The carrier body may have a through-hole, and the device holder may be replaceably fitted into the through-hole.

The device holder may be made of an elastic material.

The reference point simulator may include: a slide block coupled to the main frame to be slidable in the Y-axis direction; a simulator baseplate coupled to the slide block; and a reference point indicator provided on the simulator baseplate. The reference point indicator may be provided at a position corresponding to the brain coordinate reference point in a position in which the slide block is slide-fitted to the main frame.

The reference point indicator may have a pointed top portion protruding from the simulator baseplate.

In the position in which the slide block is slide-fitted to the main frame, the reference point indicator may be located on a straight line extending in the Y-axis direction to pass through the center of the imaginary straight line connecting the pair of ear bars, with the pointed top portion thereof being located on an XY plane.

An ear bar adaptor configured to be fixedly inserted into the ears of the primate may be detachably coupled to the pair of ear bars.

The ear bar adaptor may include: a base shaft elongated in a predetermined direction; two guide rods coupled to the base shaft to be linearly movable in an axial direction; fixing means for fixing positions of the guide rods; and ear insertion bodies provided on predetermined ends of the guide rods, respectively, to face each other.

In addition, the ear insertion bodies may have coupling recesses in predetermined ends thereof facing each other, the coupling recesses being configured to be fitted around the ear bars.

Advantageous Effects

According to the present disclosure, a brain coordinate reference point of a primate can be indicated using the simulator for indicating a brain coordinate reference point, thereby providing an initial setting to a zero point corresponding to the brain coordinate reference point. Accordingly, it is possible to conveniently and accurately indicate the brain coordinate reference point without relatively expensive equipment, such as an MRI scanner, to determine brain coordinates of a primate, so that a targeting procedure can be conducted on the brain.

In addition, the ear bar adaptor can be fixedly inserted into the ears of the primate during a process of fixing the head of the primate. It is possible to fix the head of the primate to the stereotactic device by inserting the ear bar adaptor into the ears of the primate instead of directly fixing the head of the primate to the stereotactic device. It is thereby possible to more conveniently insert the ear bars into the ears of the primate and determine whether or not the ear bars are accurately inserted in positions.

Furthermore, since the carrier body can hold a variety of brain surgery devices, it is possible to conveniently hold and replace a variety of brain surgery devices using a simple configuration without the use of a complicated additional device. Consequently, more various procedures can be more conveniently conducted.

MODE FOR INVENTION

Hereinafter, reference will be made to embodiments of the present disclosure in detail, examples of which are illustrated in the accompanying drawings. Throughout this document, reference should be made to the drawings, in which the same reference numerals and symbols will be used to designate the same or like components. In the following description of the present disclosure, detailed descriptions of known functions and components incorporated herein will be omitted in the case that the subject matter of the present disclosure may be rendered unclear thereby.

Figure 1:
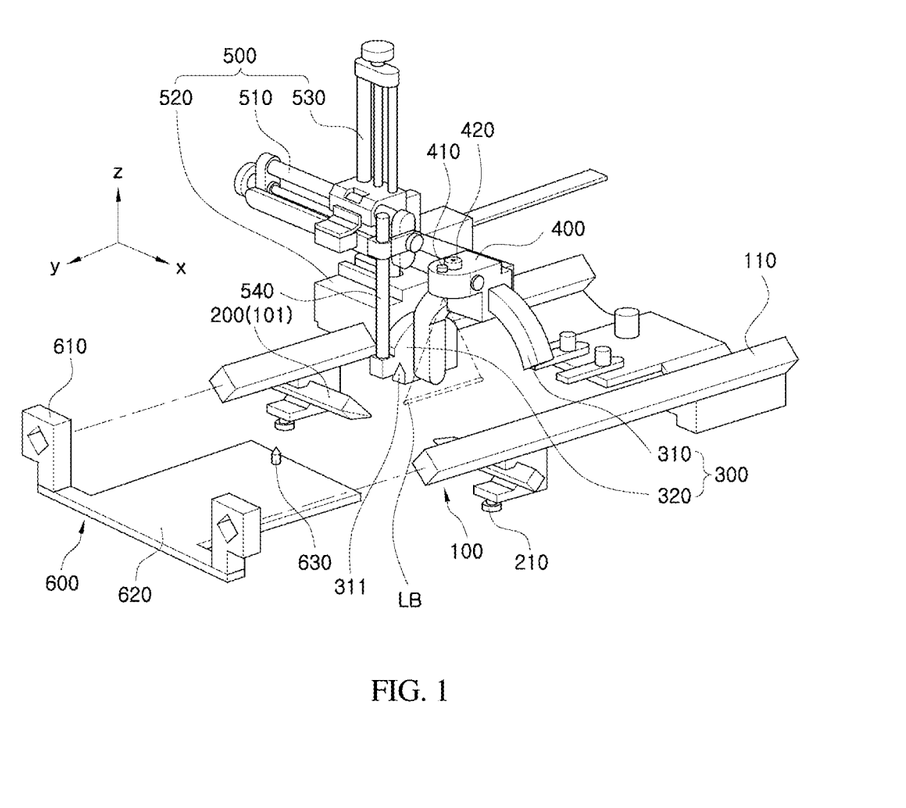
FIG. 1 is a perspective view schematically illustrating a configuration of a stereotactic device for primate brains according to exemplary embodiments.
Figure 2:
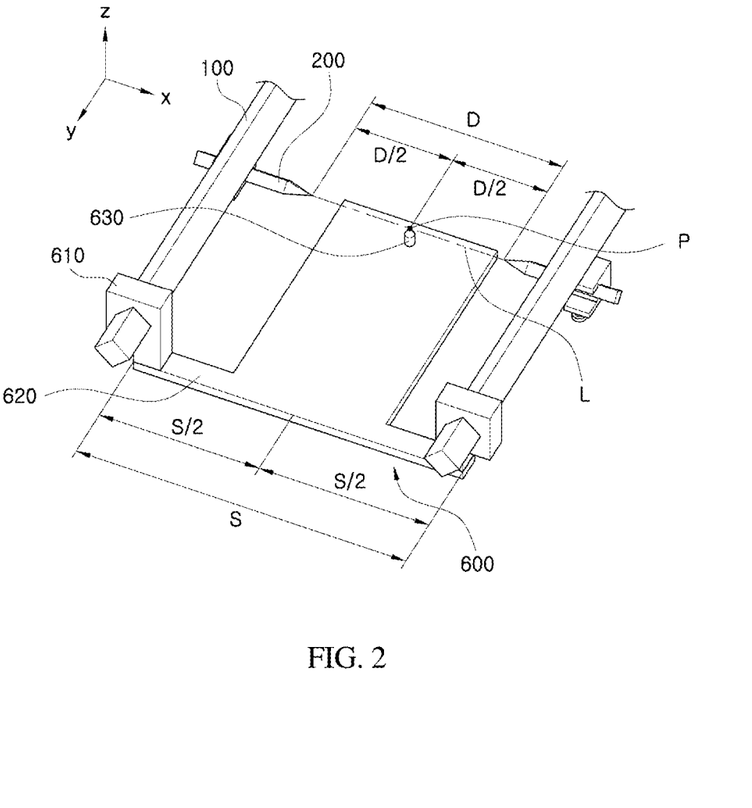
FIG. 2 is a perspective view schematically illustrating a configuration of the reference point simulator according to exemplary embodiments.
Figure 3:
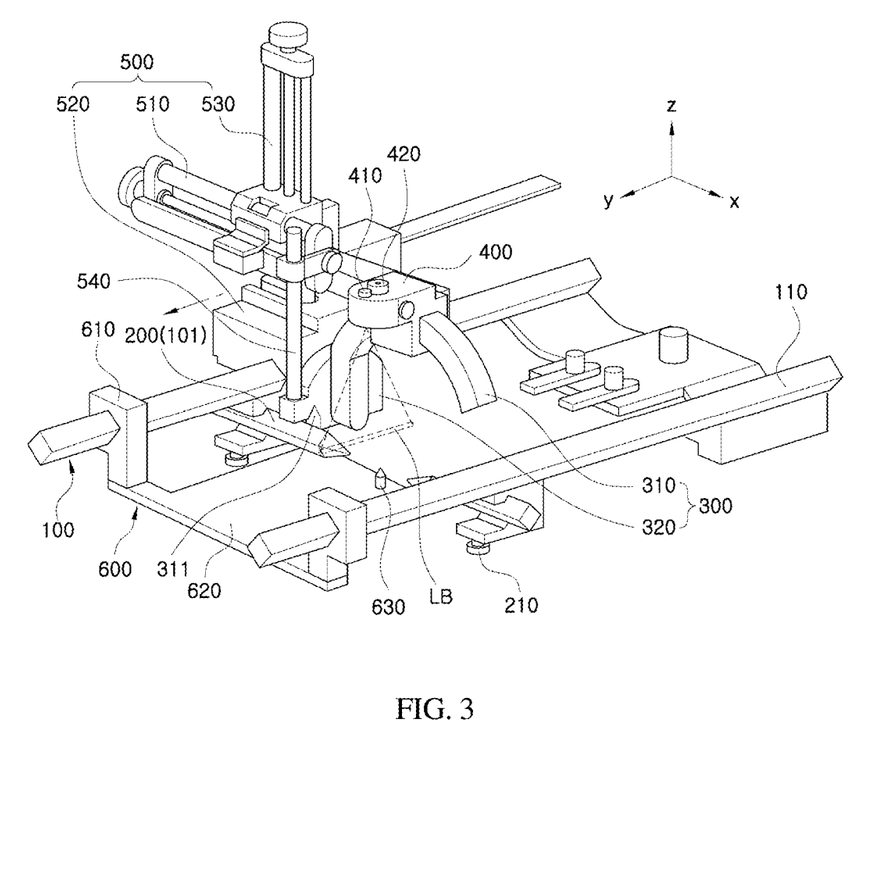
FIGS. 3 to 5 are schematic views illustrating a zero position initial setting process of the stereotactic device for primate brains according to exemplary embodiments.
Figure 4:
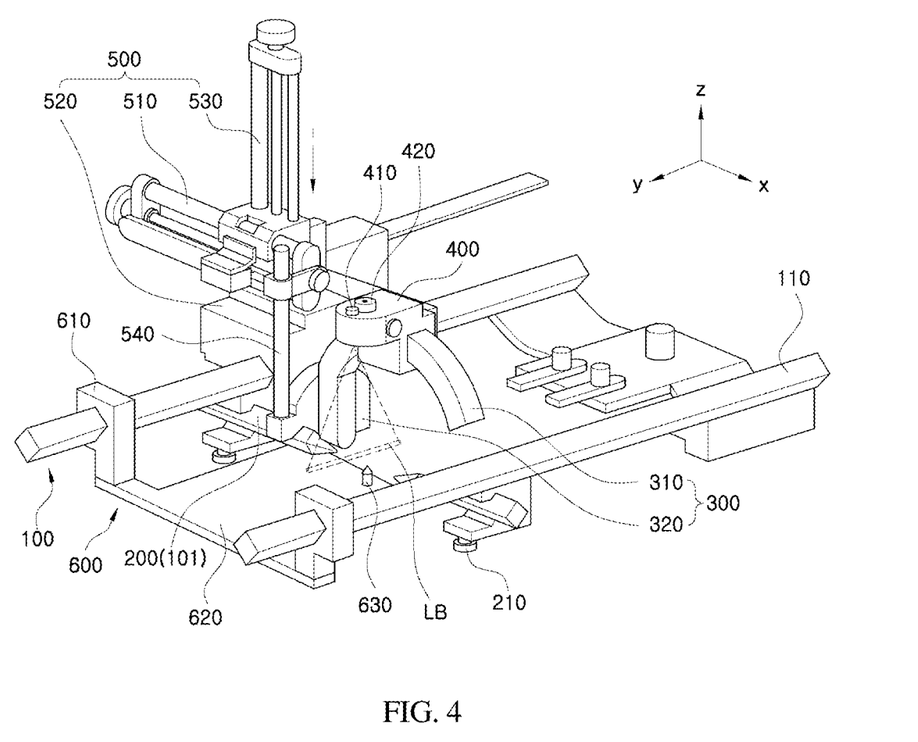
Figure 5:
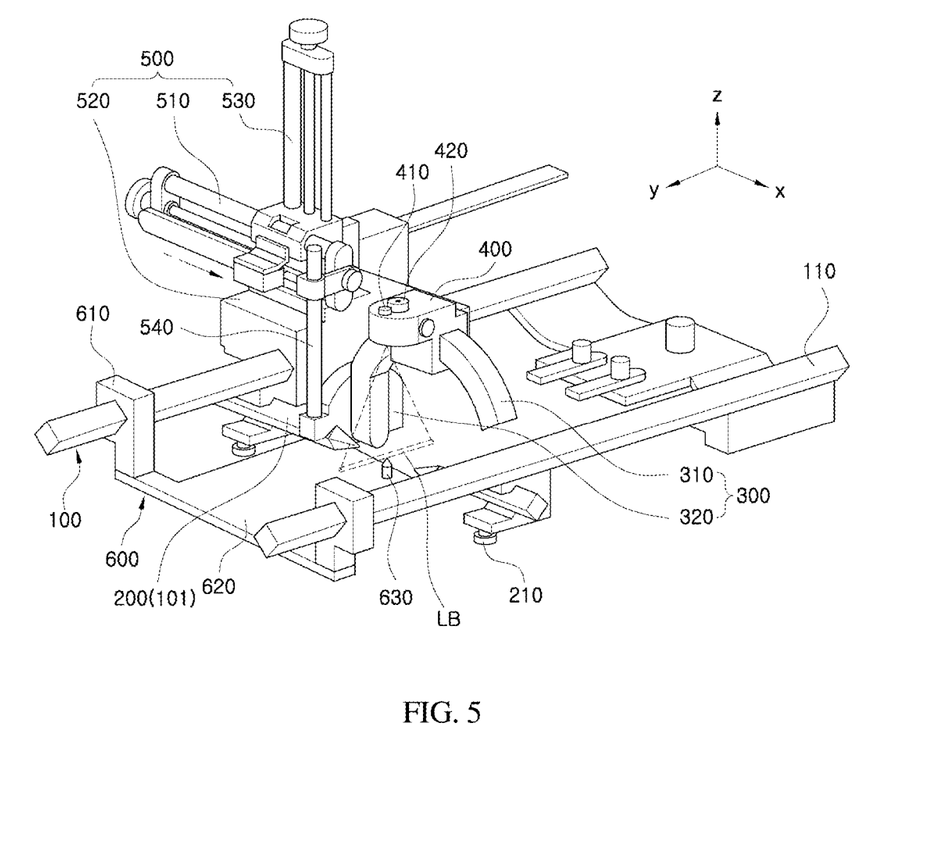

FIG. 1 is a perspective view schematically illustrating a configuration of a stereotactic device for primate brains according to exemplary embodiments, FIG. 2 is a perspective view schematically illustrating a configuration of the reference point simulator according to exemplary embodiments, and FIGS. 3 to 5 are schematic views illustrating a zero position initial setting process of the stereotactic device for primate brains according to exemplary embodiments.

The stereotactic device for primate brains according to exemplary embodiments is a device for fixing the head of a primate for an experiment or the like on a brain area of the primate, and includes a main frame 100, a pair of ear bars 200, a movable body 300, a carrier body 400, a carriage module 500, and a reference point simulator 600.

The main frame 100 provides a basic structure of the device. As illustrated in FIG. 1, the main frame 100 is configured such that support frames 110 are elongated in the Y-axis direction and are spaced apart from each other in the X-axis direction perpendicularly to the Y-axis direction.

The pair of ear bars 200 are fitted to the main frame 100 such that the ear bars 200 are spaced apart from each other while being in line in the X-axis direction. The ear bars 200 may be inserted into ears 11 of a primate 10 to fix the head of the primate 10. The ear bars 200 may be indirectly inserted into the ears 11 of the primate 10 via adaptors 700, which will be described later, although ear bars 200 may be directly inserted into the ears 11 of the primate 10.

The movable body 300 is disposed to be movable relative to the main frame 100, and is moved by the carriage module 500 in the X-axis direction, the Y-axis direction, and the Z-axis direction perpendicular to the X-axis direction and the Y-axis direction. The movable body 300 may include a movable base 310, a portion of which is coupled to the carriage module 500, and an arc portion 320 extending from the movable base 310 to provide an arc section. The arc portion 320 is provided such that a straight line extending in the X-axis direction is produced when the arc section thereof is projected onto an XY plane.

The movable base 310 may have an engagement recess 311 in a predetermined portion thereof, while the main frame 100 may have an engagement protrusion 101 on a predetermined portion thereof, configured to be inserted into and engaged with the engagement recess 311. Any one of the above-described ear bars 200 may be provided as the engagement protrusion 101, although the engagement protrusion 101 may be separately provided on the main frame 100. When the ear bars 200 are provided as the engagement protrusion 101, the engagement recess 311 of the movable base 310 are shaped such that the ear bars 200 can be inserted into and coupled to the engagement recess 311.

The carrier body 400 is connected to the movable body 300 to move integrally with the movable body 300. More specifically, the carrier body 400 is movably coupled to the arc portion 320 of the movable body 300. Accordingly, the carrier body 400 rotationally moves along a circular path of the arc portion 320. The carrier body 400 is provided with a laser projector 410 projecting a laser line beam LB in the shape of a straight line, along the Y axis. A device holder 420 may be replaceably coupled to the carrier body 400. The device holder 420 can hold a brain surgery device 20, which can be one of a variety of brain surgery devices.

The carriage module 500 is connected to the main frame 100 and, as described above, is configured to move the movable body 300 in X-axis, Y-axis, and Z-axis directions. As illustrated in FIG. 1, the carriage module 500 may include an X-axis carrier 510 moving the movable body 300 in the X-axis direction, a Y-axis carrier 520 moving the movable body 300 in the Y-axis direction, and a Z-axis carrier 530 moving the movable body 300 in the Z-axis direction. The carriers 510, 520, and 530 may respectively be implemented as a variety of mechanical elements, such as a cylinder and a linear motion (LM) guide, and may be provided in a form, the feed distance of which can be indicated in a digital format. The carriage module 500 may be provided with a coupling rod 540, which can be coupled to the movable base 310 of the movable body 300.

The reference point simulator 600 is configured to be separably inserted into the main frame 100 to indicate a brain coordinate reference point P of the primate 10, located at the center of an imaginary straight line connecting the pair of ear bars 200. The brain coordinate reference point P of the primate 10 is an ear bar zero (EBZ) point (i.e. the center of an imaginary straight line connecting the pair of ears of the primate), as described above in the Background Art section. The brain coordinate reference point P corresponds to the center P of the imaginary straight line L connecting the pair of ear bars 200, and the reference point simulator 600 is configured to indicate this point.

Described in more detail, the reference point simulator 600 includes slide blocks 610, a simulator baseplate 620, and a reference point indicator 630. The slide blocks 610 are configured to slide on the main frame 100 in the Y-axis direction. The simulator baseplate 620 is coupled to the slide blocks 610 to move integrally with the slide blocks 610. In a position in which the slide blocks 610 and the simulator baseplate 620 are slide-fitted to the main frame 100, the reference point indicator 630 is provided on the simulator baseplate 620, at a position corresponding to the brain coordinate reference point P.

The reference point indicator 630 has a pointed top portion protruding from the simulator baseplate 620. In the position in which the slide blocks 610 and the simulator baseplate 620 are slide-fitted to the main frame 100, the reference point indicator 630 is located on a Y-axis directional straight line passing through the center P of the imaginary straight line L connecting the pair of ear bars 200, with the pointed top portion thereof being located on the XY plane. Specifically, as illustrated in FIG. 2, in the position in which the simulator baseplate 620 is slide-fitted to the main frame 100, the reference point indicator 630 is located at the center of the distance D between the pair of ear bars 200, i.e. at the center of the width S of the simulator baseplate 620 in the Y-axis direction.

According to this structure, the stereotactic device for primate brains according to exemplary embodiments can indicate the brain coordinate reference point P of the primate 10 using the reference point simulator 600. Since the brain coordinate reference point P is indicated so as to be visually recognizable, it is possible to initially set the movable body 300 to a zero point corresponding to the brain coordinate reference point P by aligning the laser line beam LB of the laser emitter 410 with the brain coordinate reference point P indicate by the reference point simulator 600.

Hereinafter, the process of initially setting the movable body 300 to the zero point will be described in more detail. First, the process of initially setting the movable body 300 to the zero point includes moving the movable body 300 to a reference zero point in the X-axis, Y-axis, and Y-axis coordinates. The process of zero point setting in the Y-axis and Z-axis directions is mechanically performed using the engagement recess 311 and the engagement protrusion 101, while the process of zero point setting in the X-axis direction is performed using the laser line beam LB and the reference point simulator 600.

For example, as illustrated in FIG. 3, the movable body 300 is moved forwardly in the Y-axis direction so that the engagement recess 311 is located directly above the engagement protrusion 101. From this position, the movable body 300 may be moved downwardly in the Z-axis direction, as illustrated in FIG. 4, so that the engagement protrusion 101 is inserted into and engaged with the engagement recess 311. These operations may be performed substantially simultaneously. In response to the engagement protrusion 101 being inserted into and engaged with the engagement recess 311, the zero point of the movable body 300 can be set in the Y-axis and the Z-axis directions. Afterwards, as illustrated in FIG. 5, the zero point of the movable body 300 in the X-axis direction can be set by moving the movable body 300 to the right in the X-axis direction so that the laser line beam LB passes through the reference point indicator 630 of the reference point simulator 600.

Since the position of the movable body 300 can be set to the reference position corresponding to the brain coordinate reference point P of the primate 10 due to the above-described zero point setting, it is possible to conduct a targeting procedure on a specific location in the brain of the primate by moving the movable body 300, in the zero point reference position, based on coordinates.

Accordingly, the stereotactic device for primate brains according to exemplary embodiments allows a targeting procedure on the brains of primates to be accurately conducted without the use of an MRI scanner. Procedures and experiments on brains can be conveniently conducted without the use of relatively expensive equipment, such as an MRI scanner, and more economic experiments are possible.

Figure 6:
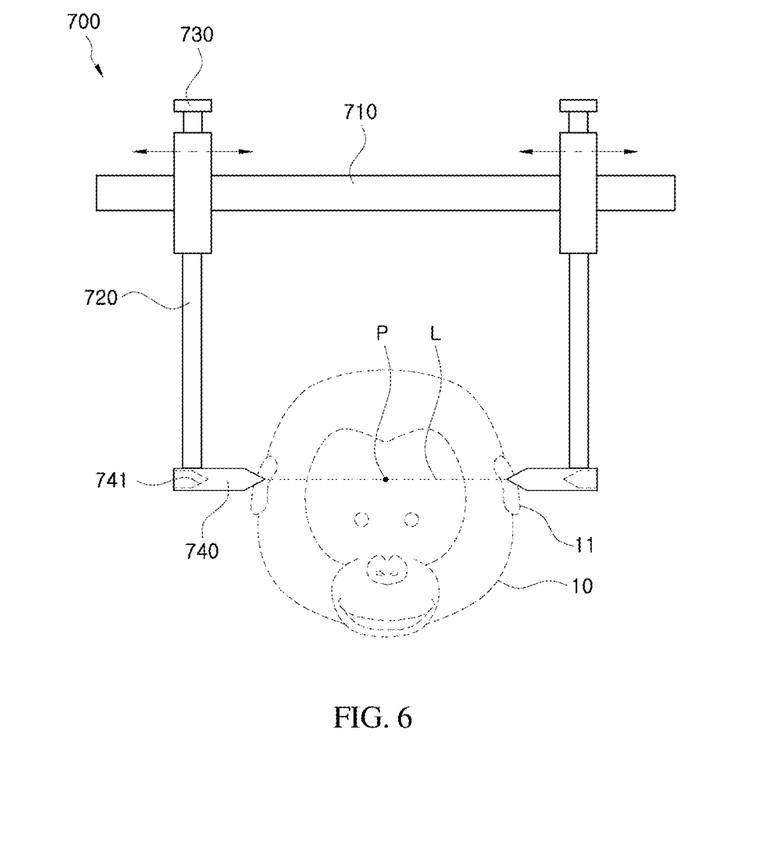
FIG. 6 is a schematic view illustrating a configuration of the ear bar adaptor according to exemplary embodiments.
Figure 7:
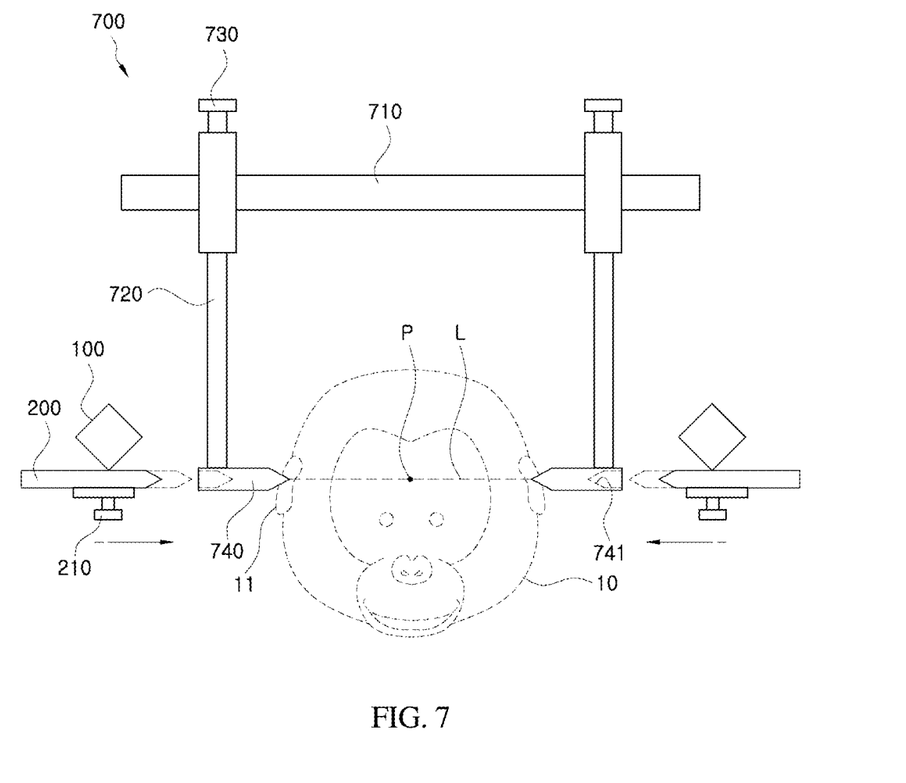
FIG. 7 is a schematic view illustrating an application of the ear bar adaptor according to exemplary embodiments.

FIG. 6 is a schematic view illustrating a configuration of the ear bar adaptor according to exemplary embodiments, and FIG. 7 is a schematic view illustrating an application of the ear bar adaptor according to exemplary embodiments.

As illustrated in FIGS. 6 and 7, the stereotactic device for primate brains according to exemplary embodiments may be provided with an ear bar adaptor 700. The ear bar adaptor 700 is a device, portions of which are to be fixedly inserted into the ears 11 of the primate 10. In a position in which portions of the ear bar adaptor 700 are inserted into the ears 11 of the primate 10, the ear bar adaptor 700 is coupled to the ear bars 200 of the main frame 100.

As illustrated in FIG. 6, the ear bar adaptor 700 includes a base shaft 710 elongated in one direction, two guide rods 720 coupled to the base shaft 710 to be linearly movable in an axial direction, fixing means 730 for fixing the positions of the guide rods 720, and ear insertion bodies 740 provided on predetermined ends of the guide rods 720, respectively, such that the ear insertion bodies 740 face each other. The ear insertion bodies 740 may be configured to be fixedly inserted into the ears 11 of the primate 10.

Coupling recesses 741 may be respectively provided in predetermined ends of the ear insertion bodies 740 facing each other. The coupling recesses 741 can be fitted around the ear bars 200.

According to this configuration, an experimenter can move the guide rods 720 towards each other by holding the ear bar adaptor 700 in one hand, so that the ear insertion bodies 740 are inserted into the ears 11 of the primates 10. In this manner, the experimenter can easily insert the ear insertion bodies 740 into both the ears 11 of the primate 10. Afterwards, when the positions of the guide rods 720 are fixed using the fixing means 730, the ear bar adaptor 700 is fixed, with the ear insertion bodies 740 being inserted into the ears 11 of the primate 10.

In this position, X-ray photography is performed to determine whether or not the insertion bodies 740 are accurately inserted. When it is determined that the insertion bodies 740 are accurately inserted, the insertion bodies 740 are maintained in this position, and the pair of ear bars 200 coupled to the main frame 100 are fixedly fitted into the insertion bodies 740, as illustrated in FIG. 7. The pair of ear bars 200 may be configured to be movable by a variety of means. For example, it is possible to move the pair of ear bars 200 in the X-axis direction using gap-adjusting means 210 or an X-axis-directional space-adjusting configuration of the main frame 100.

When the pair of ear bars 200 are fitted to the ear bar adaptor 700 inserted into the ears 11 of the primate 10, it is possible to more conveniently fix the head of the primate 10 in position than the operation of fixing the head of the primate 10 by inserting the ear bars 200 into the ears 11 of the primate 10. In particular, to fix the head of the primate 10 by inserting the ear bars 200 directly into the ears 11 of the primate 10, one person must be placed on the side of each ear of the primate. In addition, it must be determined whether or not the ear bars 200 are accurately fixed in positions. Accordingly, the operation is significantly complicated. In contrast, the use of the ear bars 700 allows the operation to be performed very simply.

Figure 8:
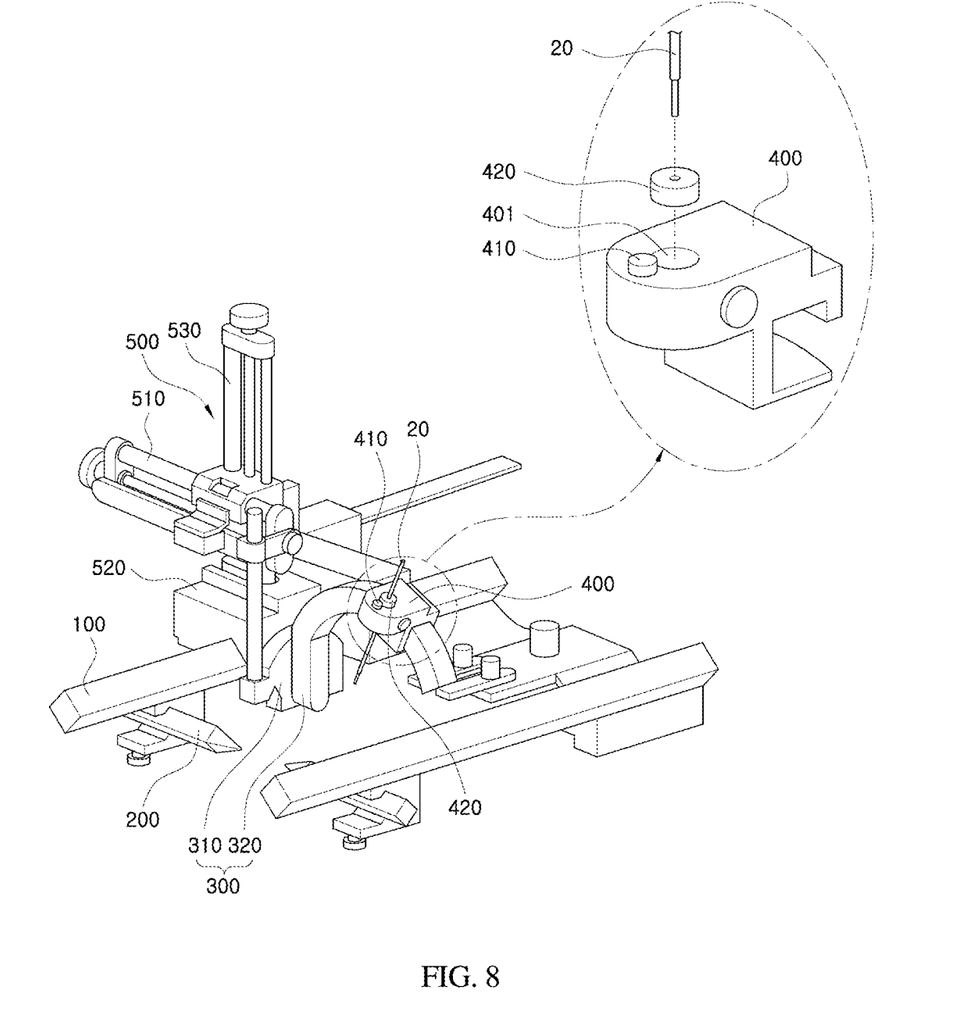
FIG. 8 is a schematic view illustrating a configuration and moved position of the carrier body according to exemplary embodiments.

FIG. 8 is a schematic view illustrating a configuration and moved position of the carrier body according to exemplary embodiments.

As described above, the carrier body 400 according to exemplary embodiments is coupled to the movable body 300 to be movable along the arc portion 320 of the movable body 300.

As described above, the carrier body 400 has the laser projector 410 for initially setting the zero point of the movable body 300. In addition, the device holder 420 for fixedly holding the brain surgery device 20 during a brain surgery on the primate is provided. The brain surgery device 20 may be one of a variety of brain surgery devices, such as an electrode probe for electrical stimulation and an injection probe for drug administration.

The device holder 420 is replaceably coupled to the carrier body 400 to hold the brain surgery device 20, which may be one of a variety of brain surgery devices. For example, a through-hole 401 may be provided in the carrier body 400, and the device holder 420 may be configured to be replaceably fitted into the through-hole 401. The device holder 420 may have some features, such as a coupling hole, corresponding to the type of the brain surgery device 20, which may be one of a variety of brain surgery devices, such that the variety of brain surgery devices can be held thereby. The device holder 420 may be made of an elastic material, such as rubber, such that the brain surgery device 20 can be tightly fitted in the coupling hole. The device holder 420 may be provided as a plurality of device holders having different shapes corresponding to types of the brain surgery devices 20.

According to this configuration, the carrier body 400 rotationally moves along the circular path of the arc portion 320 of the movable body 300, allowing a targeting procedure to be conducted on more various coordinates. In particular, rotational movement of the carrier body 400 along the arc portion 320 allows the brain surgery device 20 to be input along different paths, so that the targeting procedure can be conducted by minimizing damage to the brain organizations.

The foregoing descriptions have been presented in order to explain the certain principles of the present disclosure by way of example. A person skilled in the art to which the present disclosure relates could make various modifications and variations without departing from the principle of the present disclosure. The foregoing embodiments disclosed herein shall be interpreted as being illustrative, while not being limitative, of the principle and scope of the present disclosure. It should be understood that the scope of the present disclosure shall be defined by the appended Claims and all of their equivalents fall within the scope of the present disclosure.

DESCRIPTION OF REFERENCE NUMERALS OF DRAWINGS

100: Main frame
101: Engagement protrusion
200: Ear bar
210: Gap-adjusting means
300: Movable body
310: Movable base
311: Engagement recess
320: Arc portion
400: Carrier body
410: Laser emitter
420: Device holder
500: Carriage module
510: X-axis carrier
520: Y-axis carrier
530: Z-axis carrier
600: Reference point simulator
610: Slide block
620: simulator baseplate
630: reference point indicator
700: Ear bar adaptor
710: Base shaft
720: Guide rod
730: Fixing means
740: Ear insertion body
741: Coupling recess

The invention claimed is:

1. A stereotactic device used for brain experiments on primates, comprising:
   a main frame;
   a pair of ear bars provided on the main frame such that the ear bars are spaced apart from each other in X-axis direction, the pair of ear bars being configured to be inserted into ears of a primate to fix a head of the primate;
   a movable body disposed movable relative to the main frame;
   a carrier body connected to the movable body to move integrally with the movable body, and comprising a laser projector projecting a laser line beam, in a shape of a straight line, along a Y axis extending perpendicular to an X axis;
   a carriage module connected to the main frame to move the movable body in the X-axis direction, Y-axis direction, and Z-axis direction; and
   a reference point simulator separably inserted into the main frame to indicate a brain coordinate reference point of the primate, located at a center of an imaginary straight line connecting the pair of ear bars,
   wherein a position of the movable body is initially set to a zero point corresponding to the brain coordinate reference point, using the laser line beam generated by the laser projector and the brain coordinate reference point indicated by the reference point simulator.

2. The stereotactic device according to claim 1, wherein a zero position of the movable body in the X-axis direction is initially set by moving the movable body using the carriage module such that the laser line beam passes through the brain coordinate reference point.

3. The stereotactic device according to claim 2, wherein an engagement recess is provided in the movable body, and an engagement protrusion is fixedly provided on the main frame to be inserted into and engaged with the engagement recess,
   wherein, when the engagement recess and the engagement protrusion are engaged with each other, the engagement recess and the engagement protrusion are disposed in positions in which a zero position of the movable body in the Y-axis direction and the Z axis-direction are initially set, and
   the zero position of the movable body in the Y-axis direction and the Z axis-direction is initially set by moving the movable body using the carriage module such that the engagement recess and the engagement protrusion are engaged with each other.

4. The stereotactic device according to claim 3, wherein one of the pair of ear bars acts as the engagement protrusion.

5. The stereotactic device according to claim 4, wherein the movable body comprises a movable base, a portion of which is coupled to the carriage module, and an arc portion extending from the movable base to provide an arc section, and the engagement recess is provided in the portion of the movable base.

6. The stereotactic device according to claim 5, wherein the carrier body is movably coupled to the arc portion of the movable body.

7. The stereotactic device according to claim 6, wherein a device holder is replaceably coupled to the carrier body, and is configured to hold a brain surgery device.

8. The stereotactic device according to claim 7, wherein the carrier body has a through-hole, and the device holder is replaceably fitted into the through-hole.

9. The stereotactic device according to claim 8, wherein the device holder is made of an elastic material.

10. The stereotactic device according to claim 1, wherein the reference point simulator comprises:
    a slide block coupled to the main frame to be slidable in the Y-axis direction;
    a simulator baseplate coupled to the slide block; and
    a reference point indicator provided on the simulator baseplate,
    wherein the reference point indicator is provided at a position corresponding to the brain coordinate reference point in a position in which the slide block is slide-fitted to the main frame.

11. The stereotactic device according to claim 10, wherein the reference point indicator has a pointed top portion protruding from the simulator baseplate.

12. The stereotactic device according to claim 11, wherein, in the position in which the slide block is slide-fitted to the main frame, the reference point indicator is located on a straight line extending in the Y-axis direction to pass through the center of the imaginary straight line connecting the pair of ear bars, with the pointed top portion thereof being located on an XY plane.

13. The stereotactic device according to claim 1, wherein an ear bar adaptor configured to be fixedly inserted into the ears of the primate is detachably coupled to the pair of ear bars.

14. The stereotactic device according to claim 13, wherein the ear bar adaptor comprises;
- a base shaft elongated in a predetermined direction;
- two guide rods coupled to the base shaft to be linearly movable in an axial direction;
- fixing means for fixing positions of the guide rods; and
- ear insertion bodies provided on predetermined ends of the guide rods, respectively, to face each other.

15. The stereotactic device according to claim 14, wherein the ear insertion bodies have coupling recesses in predetermined ends thereof facing each other, the coupling recesses being configured to be fitted around the ear bars.

\* \* \* \* \*